United States Patent [19]

Brinker

[11] Patent Number: 5,592,725
[45] Date of Patent: Jan. 14, 1997

[54] TAMPON, AS WELL AS A METHOD AND A DEVICE FOR MANUFACTURING IT

[75] Inventor: Alfred Brinker, Gevelsberg, Germany

[73] Assignee: Karl Ruggli AG, Fisibach, Switzerland

[21] Appl. No.: 411,756

[22] PCT Filed: Jul. 26, 1994

[86] PCT No.: PCT/EP94/02454

§ 371 Date: May 26, 1995

§ 102(e) Date: May 26, 1995

[87] PCT Pub. No.: WO95/03766

PCT Pub. Date: Feb. 9, 1995

[30] Foreign Application Priority Data

Jul. 28, 1993 [DE] Germany ............ 43 25 220.6

[51] Int. Cl.$^6$ ............ A61F 13/20; A61B 17/52
[52] U.S. Cl. ............ 28/118; 604/904; 28/119
[58] Field of Search ............ 604/11–18, 904, 604/378, 380; 28/118, 119; 19/248; 264/320, 321

[56] References Cited

U.S. PATENT DOCUMENTS

| | | | |
|---|---|---|---|
| 2,152,230 | 3/1939 | Webb | 28/119 |
| 2,263,909 | 11/1941 | Webb | 28/119 |
| 3,422,496 | 1/1969 | Wolff et al. | 28/118 |
| 4,109,354 | 8/1978 | Ronc | 28/119 |
| 4,498,218 | 2/1985 | Friese | 28/119 |
| 4,685,178 | 8/1987 | Nakanishi | 28/118 |
| 4,951,368 | 8/1990 | Heinen | |
| 5,403,300 | 4/1995 | Howarth | 604/904 |

FOREIGN PATENT DOCUMENTS

| | | |
|---|---|---|
| 2312364 | 12/1976 | France . |
| 2623368 | 12/1976 | Germany . |
| 3606150 | 8/1987 | Germany . |
| 3934153 | 4/1991 | Germany . |

*Primary Examiner*—John G. Weiss
*Assistant Examiner*—David J. Cho
*Attorney, Agent, or Firm*— Robert W. Becker & Associates

[57] ABSTRACT

A tampon is produced rolling up a strip of fiber fleece material to form a cylindrical blank having a cylindrical mantle with mantle sections uniformly distributed over the circumference of the cylindrical blank. Pressing forces are applied to the mantle sections so as to form a preformed blank having a core and longitudinal ribs extending in the longitudinal direction of the preformed blank and distributed adjacent to one another so as to surround the core. The fiber fleece material of the core is compressed more strongly than the fiber fleece material of the longitudinal ribs. The longitudinal ribs are subjected to radial pressure forces for finish-shaping the preformed blank to form the tampon. The core of the tampon has a circular cross-section comprising an annular outer area and a circular central area surrounded by the annular outer area. The fiber fleece material of the circular central area is compressed less than the fiber fleece material of the annular outer area.

3 Claims, 4 Drawing Sheets

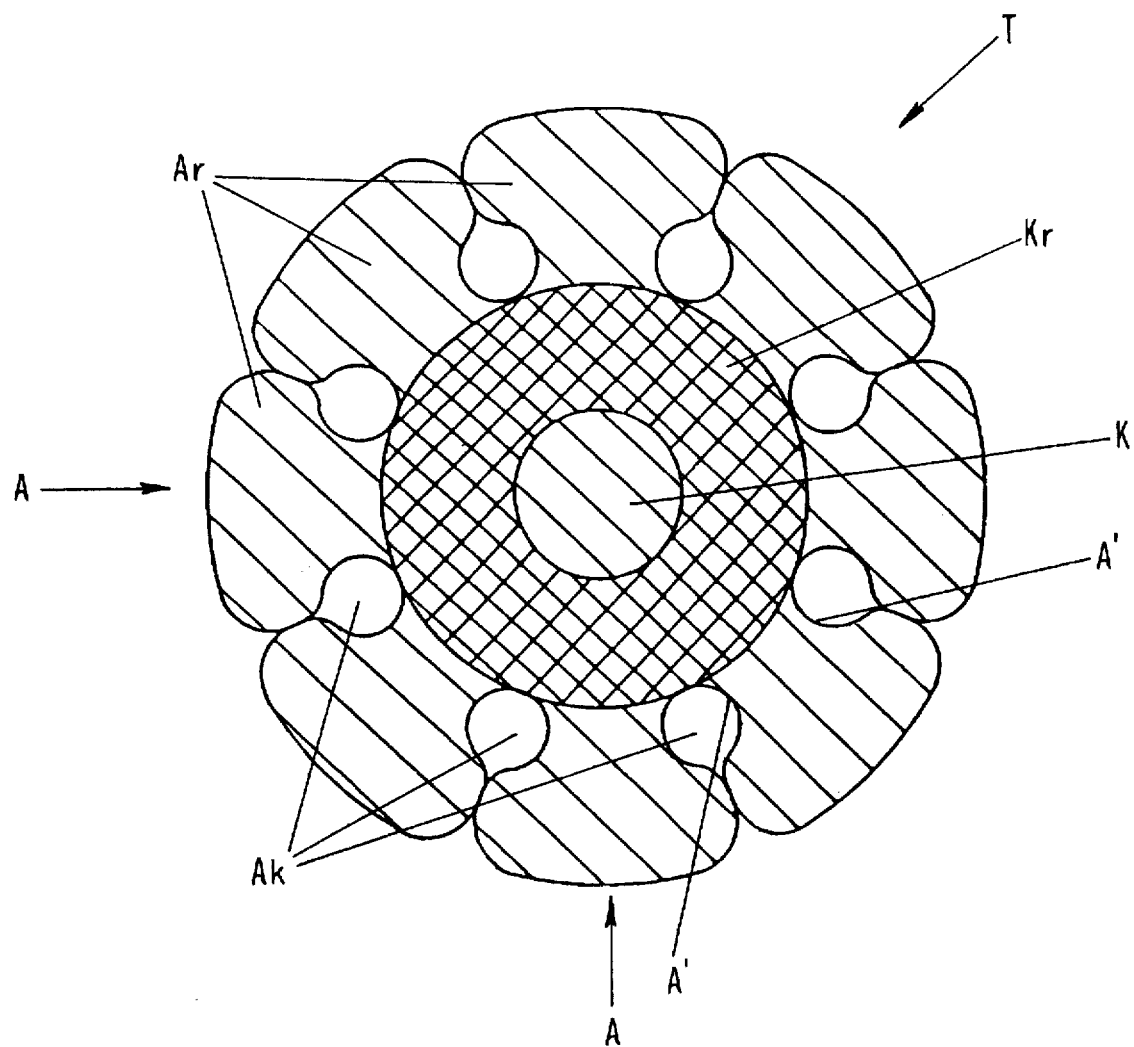
FIG — 6

TAMPON, AS WELL AS A METHOD AND A DEVICE FOR MANUFACTURING IT

BACKGROUND OF THE INVENTION

The invention relates to a tampon that is especially designed for women's hygiene and is comprised of a cylindrical blank that is manufactured by winding up a strip-shaped fiber fleece section; the blank is transformed by the application of pressing force on mantle sections that are evenly spaced about its periphery to a preformed blank with a core of higher compression of the fiber material and with longitudinal ribs of lower compression distributed around the core and which is transformed to a finished tampon by the application of radial pressure on the longitudinal ribs. Furthermore, the invention relates to a method and a device for manufacturing such a tampon.

From DE-PS 39 34 153 a tampon of the above described kind is known. In comparison with tampons that have a uniform compression throughout the entire cross-section of the tampon, this tampon has the advantage that a lower amount of material is used while still providing the same resistance to bending and the same absorbing action. The absorbing action of a tampon results from the absorbing speed which it effects and its fluid absorption capacity.

The object of the present invention is to improve a tampon as known from DE-PS 38 34 153, as well as the method and the device for manufacturing it, such that an increase of the absorbing action is possible while maintaining the resistance to bending.

SUMMARY OF THE INVENTION

A tampon, comprised of a strip of fiber fleece material rolled to a cylindrical shape, according to the present invention is primarily characterized by:

- a core of a circular cross-section, the core comprising an annular outer area and a circular central area surrounded by the annular outer area;
- longitudinal ribs extending in the longitudinal direction of the cylindrical shape, the longitudinal ribs abutting one another and distributed evenly about the circumference of the core;
- wherein each one of the longitudinal ribs has a constriction adjacent to the core such that between neighboring ones of the longitudinal ribs longitudinal channels Ak are formed that are delimited radially inwardly by the core;
- wherein the fiber fleece material of the core is compressed more strongly than the fiber fleece material of the longitudinal ribs; and
- wherein the fiber fleece material of the circular central area is compressed less than the fiber fleece material of the annular outer area.

According to a further embodiment of the present invention, the tampon is produced by a process comprising the steps of:

- rolling up a strip of fiber fleece material to form a cylindrical blank having a cylindrical mantle with mantle sections uniformly distributed over the circumference of the cylindrical blank;
- applying pressing forces onto the mantle sections and thereby forming a preformed blank having a core and longitudinal ribs extending in the longitudinal direction of the preformed blank and distributed adjacent to one another so as to surround the core, wherein the fiber fleece material of the core is compressed more strongly than the fiber fleece material of the longitudinal ribs; and
- subjecting the longitudinal ribs to radial pressure forces for finish-shaping the preformed blank to form the tampon, wherein the core of the tampon has a circular cross-section comprising an annular outer area and a circular central area surrounded by the annular outer area, wherein the fiber fleece material of the circular central area is compressed less than the fiber fleece material of the annular outer area.

The present invention also relates to a method of manufacturing a tampon. The inventive method is characterized by the steps of:

- rolling up a strip of fiber fleece material to form a cylindrical blank having a cylindrical mantle with mantle sections uniformly distributed over the circumference of the cylindrical blank;
- applying pressing forces onto the mantle sections, wherein the pressing forces are directed tangentially relative to a circular cylinder surrounding a central axis of the blank at a selected distance, and thereby forming a preformed blank having a core and longitudinal ribs extending in the longitudinal direction of the preformed blank and distributed adjacent to one another so as to surround the core, wherein the fiber fleece material of the core is compressed more strongly than the fiber fleece material of the longitudinal ribs; and
- subjecting the longitudinal ribs to radial pressure forces for finish-shaping the preformed blank to form the tampon, wherein the core of the tampon has a circular cross-section comprising an annular outer area and a circular central area surrounded by the annular outer area, wherein the fiber fleece material of the circular central area is compressed less than the fiber fleece material of the annular outer area.

The present invention also relates to a device for manufacturing a tampon. The inventive device comprises:

- a preforming device comprising a receiving opening for a tampon blank and pressing tools for compressing the tampon blank, received in the receiving opening, to a preformed blank having a mantle area with longitudinal ribs;
- the preforming device further comprising for each one of the pressing tools a lever pivotable about a pivot axis between two end positions and having an inner end proximal to the receiving opening and an outer end distal to the receiving opening, the pressing tools connected to the inner end of the levers; and
- a shaping tool for finish-shaping the preformed blank to form the finished tampon.

Preferably, the pivot axis is a bearing pin.

The preforming device further comprises a ring bearing and a coupling lever for each one of the levers, wherein the outer end of each one of the levers is connected with one of the coupling levers to the ring bearing. An adjusting ring is provided, and each one of the levers is connected to the adjusting ring with the bearing pin so as to be pivotable relative to the adjusting ring.

Each one of the pressing tools is advantageously detachably connected to the lever in order to be exchangeable.

Each one of the pressing tools preferably comprises a projecting pressing edge.

The tampon that resolves this object according to the invention is characterized in that the core is formed by a cross-sectionally annular area of highest compression and a central area of medium compression which is located within this annular area.

By replacing a core that is uniformly comprised of highly compressed fiber fleece material with a cross-sectionally annular area of highest compression and a central area of medium compression within this annular area, the form stiffness of the tampons is maintained, on the one hand, since the annular cross-section of fiber material of highest compression has essentially the same geometrical movement of inertia and thus in connection with the central area of medium compression has the same stiffness as a core of uniform compression. On the other hand, however, at least the same absorbing action is achieved by the lower compression of the fiber material in the central area of the tampon despite the lower amount of material used since the absorption volume is maintained and the absorbing speed in the central area is increased by its higher capillary action.

The inventive method is carried out according to the known prior art by transforming the blank that is comprised of wound-up strip-shaped fiber fleece material to a preformed blank as a result of the application of pressing forces on mantle sections that are spaced from one another and by finish-shaping the preformed blank that is provided with longitudinal ribs by applying radial pressure. The inventive development of this method is characterized in that the pressing forces are directed tangentially toward a circular cylinder that surrounds the longitudinal center axis of the tampon at a selected distance.

The eccentric application of the pressing forces on the blank according to the inventive method results in that, instead of a core with a uniform compression, a cross-sectionally annular area of highest compression and a central area of medium compression are formed. The orientation of the pressing forces, which is different than the one of the known method, thus leads to the manufacture of the inventive tampon without any greater complications.

The device for manufacturing a tampon according to the invention comprises, in accordance with the known device, a number of pressing tools for comprising the blanks in the core area and for creating longitudinal ribs in the mantle area, as well as a shaping tool for finish-shaping the tampon. For resolving the object of the invention, the device is characterized in that the pressing tools are each arranged at the inner end of a lever that is pivotable about a pivot axis between two end positions. In a simple way the arrangement of the pressing tools at the inner end of levers creates the possibility to direct the pressing forces required for the production of the inventive tampon, respectively, required to carry out the inventive method such that they are tangentially directed toward a circular cylinder that surrounds the longitudinal center axis of the tampon at a selected distance. This result in a sectioning of the core into a cross-sectionally annular area of highest compression and a central area of lower compression which is located within this annular area.

With a prefered embodiment of the inventive device each lever is supported at its outer end by a ring bearing via a coupling lever and is pivotable by an adjusting ring at which the levers are each rotatably supported by a bearing pin. This results in a particularly simple construction.

According to further features of the invention it is suggested to arrange the pressing tools replaceably at the levers and to provide them with projecting pressing edges to produce longitudinal ribs of a lower compression radially outside of the cross-sectionally annular area of highest compression and longitudinal channels which are located between these ribs and which increase, when the tampon is finish-shaped, the absorbing action of the tampon in the outer area in the manner of chambers.

BRIEF DESCRIPTION OF THE DRAWING

In the drawings an embodiment of the tampon and a device for manufacturing it are illustrated. It is illustrated in.

DESCRIPTION OF PREFERRED EMBODIMENTS

Figure 1:
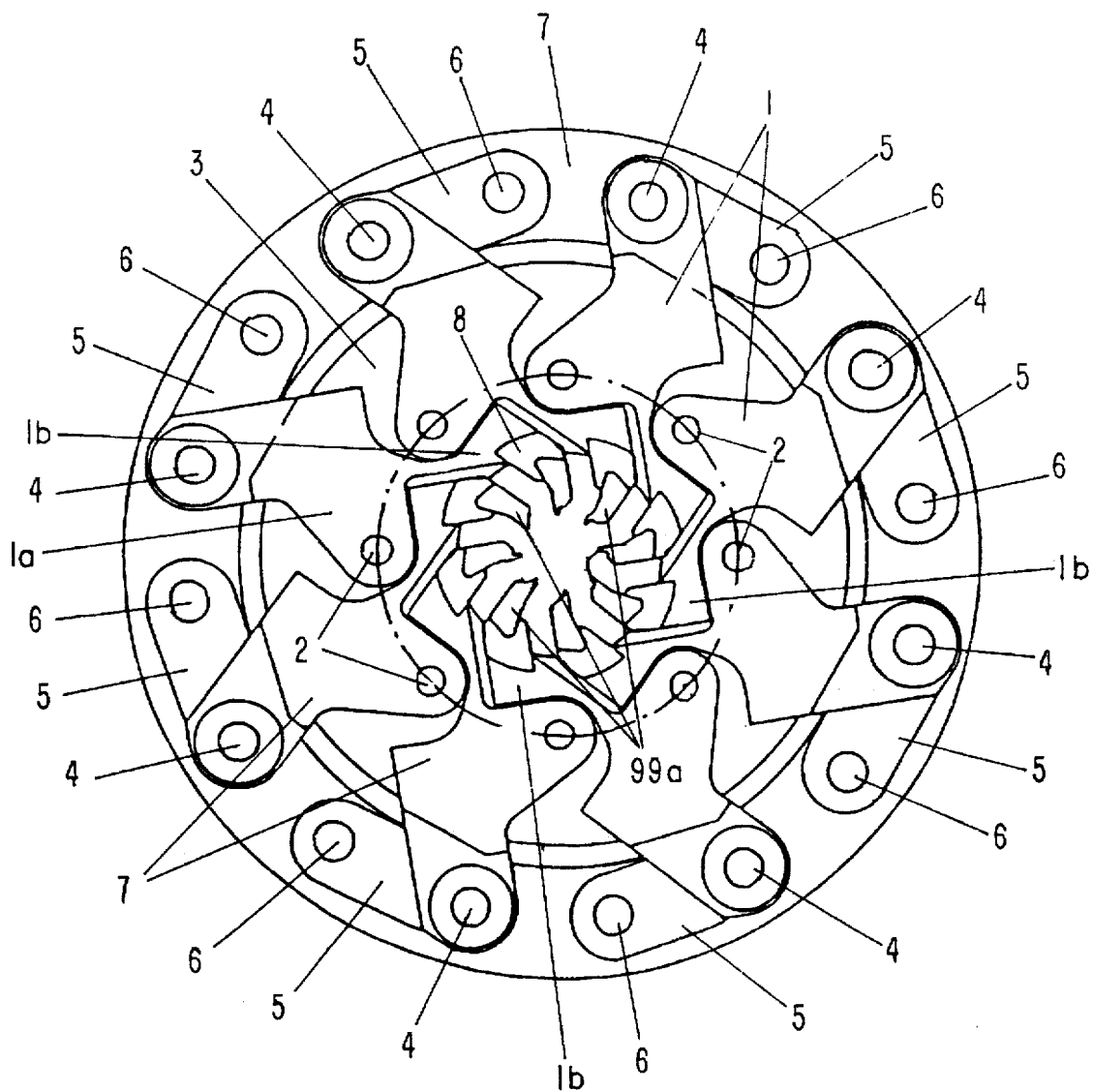
FIG. 1 a device for manufacturing a preformed blank as a part of a machine for manufacturing a tampon, FIG. 2 the central portion of the device in the open starting position, FIG. 3 the central portion of the device in an intermediate position, FIG. 4 the central portion of the device in the closed end position, FIG. 5 a cross-section through a tampon, and FIG. 6 a schematic illustration of the cross-section of a tampon according to FIG. 5.

The embodiment of a device for manufacturing a tampon that is illustrated in FIG. 1 comprises eight levers 1 each supported at an adjusting ring 3 and pivotable within certain limits about a bearing pin 2. At its radially outer end each lever 1 is pivotably linked by a coupling pin 4 to a coupling lever 5 the other end of which is pivotably supported by means of a pin 6 at a stationary ring bearing 7. The pins 6 as well as the bearing pins 2 are each positioned on a circle, whereby the spacing of these bolts toward one another is a result of the sectioning specified by the number of the levers 1 on the respective circle.

The levers 1, which are designed as an angle levers and which are provided with a projecting portion 1a between their support location by the pin bearing 2 on the adjusting ring 3 and their articulation by a coupling pin 4 on the coupling lever 5, furthermore comprise a lever arm 1b that is positioned radially inwardly and supports at its end portion that is positioned radially inwardly a tool carrier 8 to which a pressing tool 9 is attached. Each pressing tool 9 is provided with a pressing edge 9a that is illustrated in the center of FIG. 1.

By rotating the adjusting ring 3 that is concentrically arranged with respect to the stationary ring bearing 7, a swiveling of the lever 1 is caused. On rotating the adjusting ring 3 counterclockwise these levers 1 are, according to FIG. 1, moved radially inwardly with their pressing tools 9. Thus, the levers 1 swivel about the bearing pins 2 which are arranged at the adjusting ring 3 whereby the coupling pins 4 that are connected with the ring bearing 7 via the coupling levers 5 produce the swiveling movement which results in a radially inwardly directed movement of the pressing tools 9. Thus, a "closing" of the pressing tools 9 is performed. When the adjusting ring 3 is rotated clockwise, an "opening" of the pressing tools 9 is accordingly performed.

Figure 2:
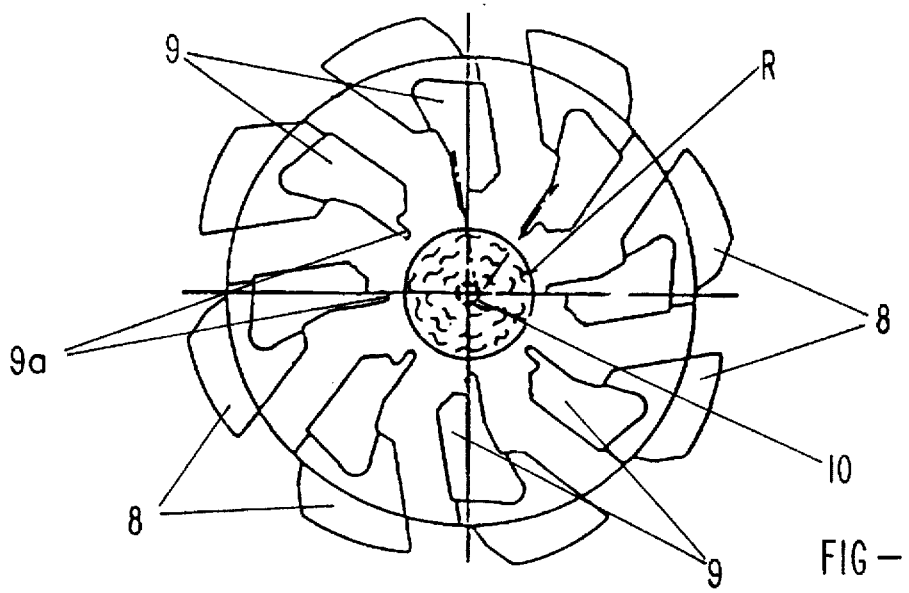

FIG. 2 illustrates that in the open starting position the pressing edges 9a of the pressing tools 9 are not directed toward the center of the device but tangentially toward a circular cylinder 10 that surrounds the longitudinal center axis at a selected distance. This circular cylinder 10 is illustrated dash-dottedly in FIG. 2. Thus it is achieved that the pressing forces which are applied by the pressing tools 9 are not centrally but tangentially directed toward a circle that surrounds the longitudinal center axis of the tampon to be manufactured at a selected distance. This eccentric orientation of the pressing edges 9a toward the central point of the device can be adjusted to any desired position by respectively positioning the bearing pin 2 and by providing a corresponding design of the levers 1 as well as of the coupling levers 5.

Figure 3:
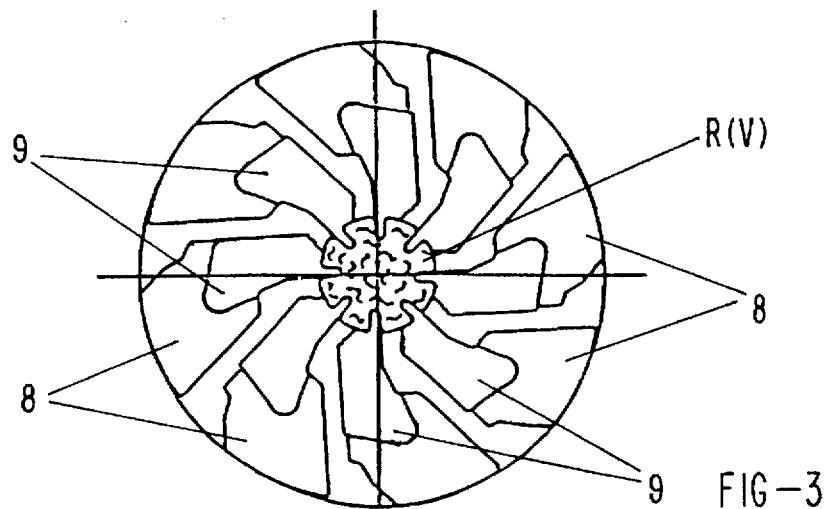
Figure 4:
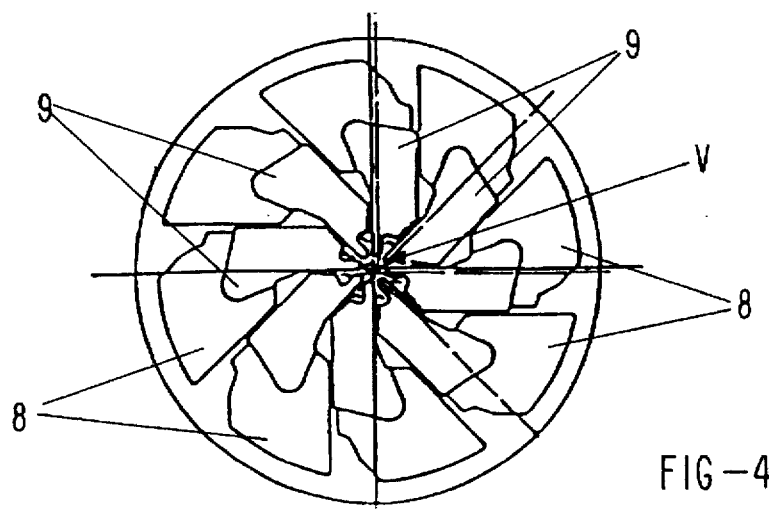

In the open starting position of the device according to FIG. 2 a cylindrical blank R is inserted into the opening between the pressing tools 9. This blank R was manufactured by winding up a strip-shaped fiber fleece section. By rotating the adjusting ring 3 counterclockwise relative to the stationary ring bearing 7, the pressing tools 9 are first brought into the intermediate position illustrated in FIG. 3 and finally into the end position illustrated in FIG. 4. With this swiveling movement, the levers 1 are, on the one hand, moved with the adjusting ring 3, and, on the other hand, are swiveled about the bearing pins 2 of the rotating adjusting ring 3 by the coupling levers 5 that are articulated at the stationary ring bearing 7 such that the pressing tools 9 perform a movement combined of a tangential and a radial component. A comparison of FIG. 3 and 4 with FIG. 2 shows that during this movement the deformation forces which are applied by the pressing tools 9 and their pressing edges 9a lead to a volume reduction of the blank R that is uniform about the periphery and transform the blank R into a preformed blank V (see FIG. 4) having a core and longitudinal ribs which surround the core. Such a preformed blank is illustrated in an enlarged view in FIG. 5. After slightly opening the pressing tools 9, the preformed part V is removed from the device and is finish-shaped into a tampon during the subsequent processing steps by the application of radial pressure on the longitudinal ribs.

Figure 5:
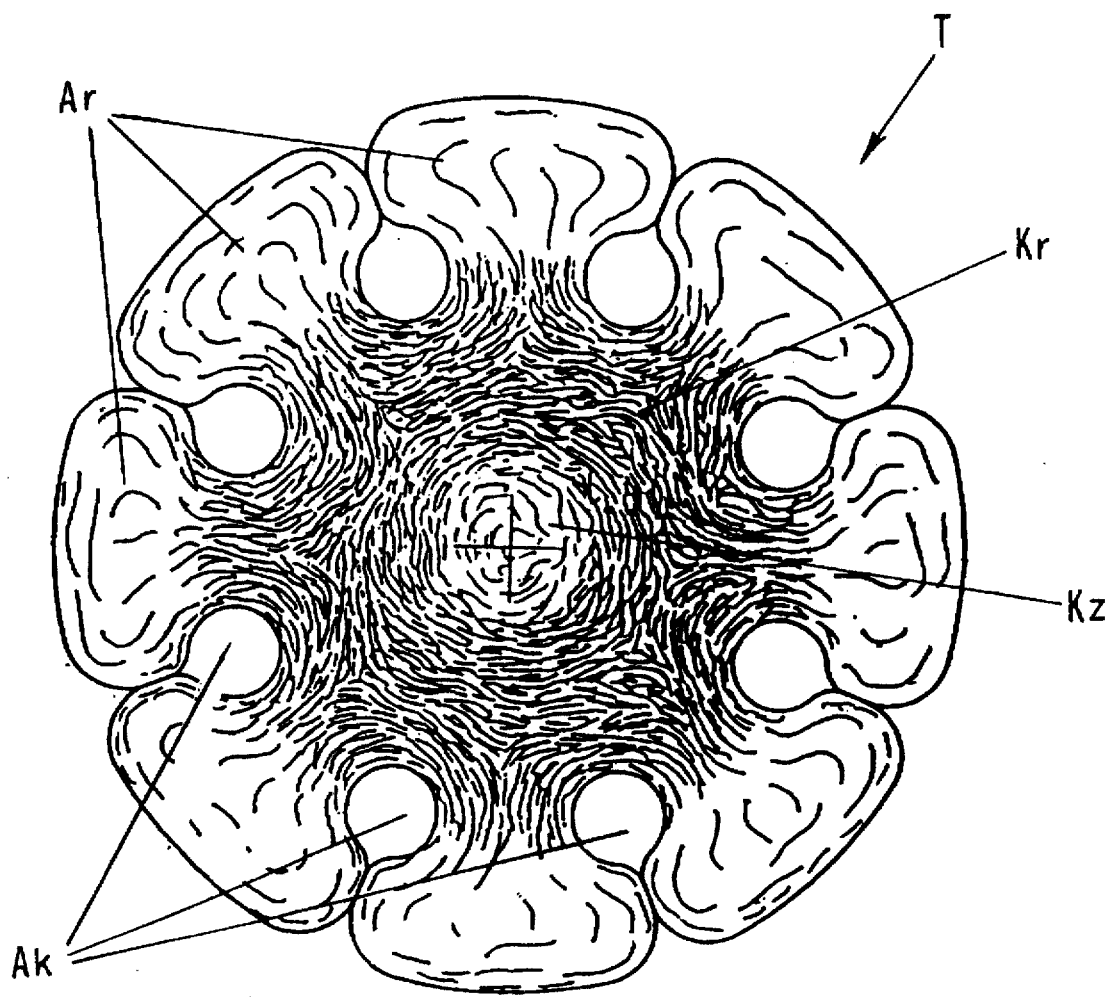

FIG. 5 illustrates a cross-section through a finished tampon T. It comprises a core area with different compression areas, namely an annular area Kr of highest compression as well as a central area Kz of medium compression. This core area is surrounded by an outer area Ar created by the deformation of the ribs of the preformed part V thereby enclosing channels Ak which extend in the longitudinal direction of the tampon. In the outer area Ar that was formed by deforming the ribs of the preformed part V, the lowest compression of the fiber fleece material is encountered. In the annular area Kr the highest compression follows; in the central area Kz a medium compression is encountered.

These different compressions of the finished tampon T are additionally illustrated schematically in FIG. 6 with the aid of a cross-section of a tampon. The annular area Kr has the highest compression, the central area Kz that is located within this annular area Kr has a medium compression, whereas the fiber fleece material in the outer area Ar has the lowest compression. The schematic illustration in FIG. 6 shows that by this design of the tampon which is created by the tangential orientation of the pressing forces on a circular cylinder that surrounds the longitudinal center axis of the tampon at a selected distance the following advantages are achieved: by the annular area Kr of highest compression the tampon T, on the one hand, gains a high form stiffness, particularly a resistance to bending. The tampon T comprises as well an integrated tube, as is illustrated by the double hatched area in FIG. 6. On the other hand, the lower compressed central area Kz can be utilized for receiving body fluid that is very quickly absorbed by the tampon due to the presence of the longitudinally extending channels Ak and transported via the circular area Kr into the central area Kz that performs a certain absorbing action due to its medium compression.

The present invention is, of course, in no way restricted to the specific disclosure of the specification and drawings, but also encompasses any modifications within the scope of the appended claims.

What I claim is:

1. A method of manufacturing a tampon, said method comprising the steps of:

rolling up a strip of fiber fleece material to form a cylindrical blank having a cylindrical mantle with mantle sections uniformly distributed over the circumference of the cylindrical blank;

applying pressing forces onto the mantle sections, wherein the pressing forces are directed tangentially relative to a circular cylinder surrounding a central axis of the blank at a selected distance, and thereby forming a preformed blank having a core and longitudinal ribs extending in the longitudinal direction of the preformed blank and distributed adjacent to one another so as to surround the core, wherein the fiber fleece material of the core is compressed more strongly than the fiber fleece material of the longitudinal ribs; and subjecting the longitudinal ribs to radial pressure forces for finish-shaping the preformed blank to form the tampon, wherein the core of the tampon has a circular cross-section comprising an annular outer area and a circular central area surrounded by the annular outer area, wherein the fiber fleece material of the circular central area is compressed less than the fiber fleece material of the annular outer area.

2. A tampon, comprised of a strip of fiber fleece material rolled to a cylindrical shape, said tampon comprising:

a core of a circular cross-section, said core comprising an annular outer area and a circular central area surrounded by the annular outer area;

longitudinal ribs extending in the longitudinal direction of the cylindrical shape, said longitudinal ribs abutting one another and distributed evenly about the circumference of the core;

wherein each one of said longitudinal ribs has a constriction adjacent to said core such that between neighboring ones of said longitudinal ribs longitudinal channels are formed that are delimited radially inwardly by said core;

wherein the fiber fleece material of the core is compressed more strongly than the fiber fleece material of the longitudinal ribs; and wherein the fiber fleece material of the circular central area is compressed less than the fiber fleece material of the annular outer area.

3. A tampon produced by a process comprising the steps of:

rolling up a strip of fiber fleece material to form a cylindrical blank having a cylindrical mantle with mantle sections uniformly distributed over the circumference of the cylindrical blank;

applying pressing forces onto the mantle sections and thereby forming a preformed blank having a core and longitudinal ribs extending in the longitudinal direction of the preformed blank and distributed adjacent to one another so as to surround the core, wherein the fiber fleece material of the core is compressed more strongly than the fiber fleece material of the longitudinal ribs; and subjecting the longitudinal ribs to radial pressure forces for finish-shaping the preformed blank to form the tampon, wherein the core of the tampon has a circular cross-section comprising an annular outer area and a circular central area surrounded by the annular outer area, wherein the fiber fleece material of the circular central area is compressed less than the fiber fleece material of the annular outer area.

* * * * *